United States Patent [19]

Hauze

[11] Patent Number: 4,813,931
[45] Date of Patent: Mar. 21, 1989

[54] PEDIATRIC SUCTION SYSTEM AND METHOD WITH FILTER

[75] Inventor: Dennis R. Hauze, Bountiful, Utah
[73] Assignee: Tre Med, Inc., Houston, Tex.
[21] Appl. No.: 901,755
[22] Filed: Aug. 28, 1986
[51] Int. Cl.⁴ ............................................. A61M 31/00
[52] U.S. Cl. ........................................ 604/54; 604/73; 604/276; 604/319; 128/760
[58] Field of Search .............. 128/760, 767, 768, 771, 128/207.14, 207.16, 206.11, 203.11, 202.29, 202.28, 205.29, 206.22; 604/205.18, 201.25, 205.19, 54, 73, 76, 118, 119, 128, 133, 181, 183, 185, 186, 275, 276, 278, 313–319, 902, 320, 321

[56] References Cited

U.S. PATENT DOCUMENTS

| | | | |
|---|---|---|---|
| 2,522,108 | 9/1950 | Flagg | 604/319 |
| 2,700,973 | 1/1955 | Ju | 128/771 |
| 3,057,347 | 10/1962 | McGee | 128/202.28 |
| 3,175,557 | 3/1965 | Hammond | 128/207.14 |
| 3,224,434 | 12/1965 | Molomut et al. | 128/760 |
| 4,275,724 | 6/1981 | Behrstock | 128/207.14 |
| 4,317,525 | 3/1982 | Schuessler et al. | 604/73 |
| 4,347,946 | 9/1982 | Nichols | 604/119 |
| 4,459,139 | 7/1984 | VonReis et al. | 604/320 |
| 4,507,120 | 3/1985 | Pardis | 604/320 |
| 4,516,973 | 5/1985 | Telang | 604/319 |
| 4,643,197 | 2/1987 | Greene et al. | 604/319 |
| 4,662,367 | 5/1987 | Gore, Jr. | 604/73 |
| 4,685,472 | 8/1987 | Muto | 128/760 |

OTHER PUBLICATIONS

"The Lancet", vol. II 164, No. 7349, Jul. 4, 1964, p. 21, by M. Marshall.
J. Thoracic and Cardiovascular Surg., vol. 57, No. 5, May 1969.

Primary Examiner—John D. Yasko
Assistant Examiner—Mario Costantino
Attorney, Agent, or Firm—J. Winslow Young

[57] ABSTRACT

This invention relates to a novel, pediatric suction system and method whereby a liquid-impervious filter prevents liquids aspirated into the chamber through a suction tube from traveling into a vacuum tube. Correspondingly, the filter prevents reverse travel of contaminants from the vacuum tube to the suction tube. The filter is liquid impervious and porous with sufficient porosity so as to not interfere with the sensitivity of a partial vacuum applied to the vacuum tube by a physician. The suction tube and vacuum tubes are releasably connected to the container and provision is made for transport of the aspirated liquids.

4 Claims, 3 Drawing Sheets

PEDIATRIC SUCTION SYSTEM AND METHOD WITH FILTER

BACKGROUND

1. Field of the Invention

This invention relates to pediatric suction systems and, more particularly, to novel improvements in pediatric suction systems whereby a liquid-impervious filter serves as a blockage means in the pediatric suction system to prevent aspiration of liquids by the operator upon application of oral suction to the suction system.

2. The Prior Art

Recent advances have been made in delivery room resuscitation of infants by meconium aspiration to remove fluids. This procedure clears the oropharynx so as to substantially reduce infant morbidity and mortality with few complications for the neonate. One common practice is to insert an orotracheal tube below the infant's vocal cords and apply oral suction through a face mask while withdrawing the tube. Another procedure involves the additional use of a DeLee catheter (usually used with direct oral suction) to clear the oropharynx while the infant's head is still on the perineum.

Oral suction applied directly to an unmasked endotracheal tube, a tilted or overfilled DeLee suction apparatus, or to a mask moistened by secretions from the endotracheal tube represents an opportunity for the exchange of potentially harmful organisms. Recent cases have been reported where the transmission of herpes virus type I from an infected physician to a meconium-stained infant occurred during mouth-to-tube suctioning through a mask. Other reports document physician exposure to culture-documented, pathogenic organisms while performing oral endotracheal suctioning on meconium-stained infants in the delivery room. Accidental suction of this material into the mouth of the operator is also extremely distasteful and unpleasant.

The organisms, immediate symptoms and subsequent treatment are discussed in detail in "Hazards of Delivery Room Resuscitation Using Oral Methods of Endotracheal Suctioning," *Pediatric Infectious Disease*, Vol. 5, No. 2, (1986) J. L. Ballard, M.D.; M. J. Musial, R.N.; and M. G. Myers, M.D. Of the incidents reported, four physicians syphoned the pathogen-containing secretions into their mouths. One asymptomatic physician ingestor recovered a "heavy growth" of *Neisseria gonorrheae* from his throat prior to receiving benzathine penicillin. Another developed a sore throat with fever and malaise after ingesting *Haemophilus influenzae*.

A summary of the prior art reveals that although the mouth-to-tube method of resuscitation has proved efficacious in removing meconium from the neonatal airway, theoretical risks appear to exist for the resuscitating physician and possibly for the neonate. It would, therefore, be a significant advancement in the art to provide a pediatric suction apparatus and method wherein a blocking mechanism is provided to preclude the aspiration by the physician of fluids from the neonate and, correspondingly, to preclude the transfer of pathogenic organisms from the physician to the neonate. It would also be an advancement in the art to provide a pediatric endotracheal suction catheter system which can be used with various sizes of suction tubes and which includes a specimen collection container to facilitate transportation of the aspirated fluids to the laboratory for subsequent testing and analysis. Such a novel apparatus and method is disclosed and claimed herein.

BRIEF SUMMARY AND OBJECTS OF THE INVENTION

The present invention relates to a novel, pediatric suction system and method whereby a collection container is provided for receiving fluids aspirated from the neonate. The container includes a suction tube at one position and the vacuum tube at another position with a blocking mechanism consisting of a liquid-impervious filter interposed between the suction tube and the vacuum tube. The container also includes cap mechanisms for retaining aspirated fluids in the container so that the container can serve as a specimen handling device. The blockage mechanism is prepared from a commercially available liquid-impervious filter that prevents the passage of liquids into the vacuum tube during suction which causes the inflow of aspirated fluids into the collection container.

It is, therefore, a primary object of this invention to provide improvements in pediatric suction systems.

Another object of this invention is to provide an improved method for aspirating fluids with a pediatric suction system.

Another object of this invention is to provide a pediatric suction system having a blockage means interposed between the suction tube and the vacuum tube.

Another object of this invention is to provide a collection container for liquids aspirated through the suction tube, the container including indicia for indicating the volume of liquids aspirated into the container.

Another object of this invention is to provide a novel, liquid-impervious filter in or adjacent the vacuum tube to thereby preclude exchange of organisms and liquids between the collection container and the vacuum tube.

These and other objects and features of the present invention will become more fully apparent from the following description and appended claims taken in conjunction with the accompanying drawing.

DETAILED DESCRIPTION OF THE PREFERRED EMBODIMENTS

Figure 1:
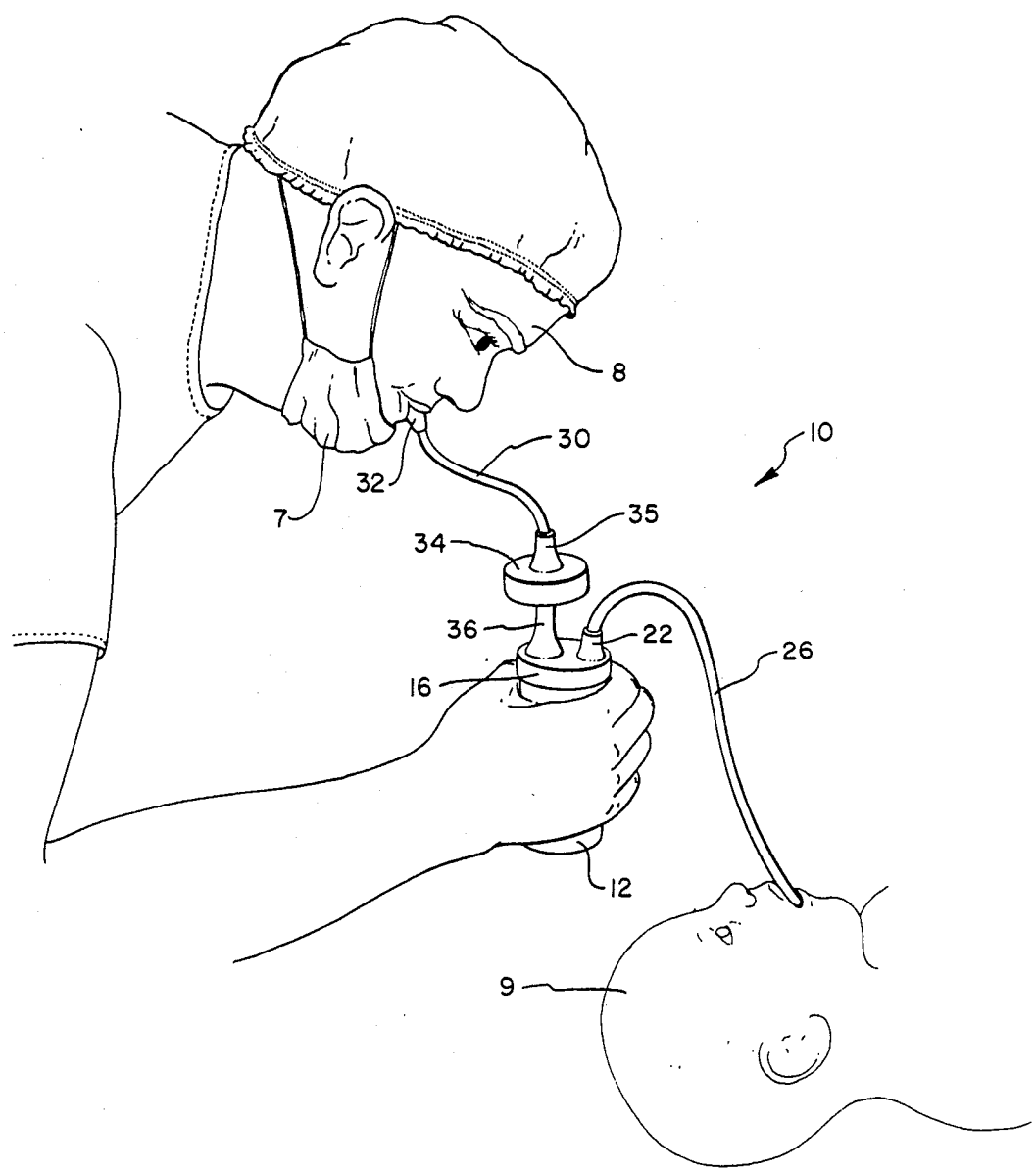
FIG. 1 is a schematic illustration of the novel pediatric endotracheal suction system of this invention shown in the environment of an operator and a patient.

The novel apparatus and method of this invention is best understood by reference to the drawing wherein like parts are designated by like numerals throughout.

Figure 2:
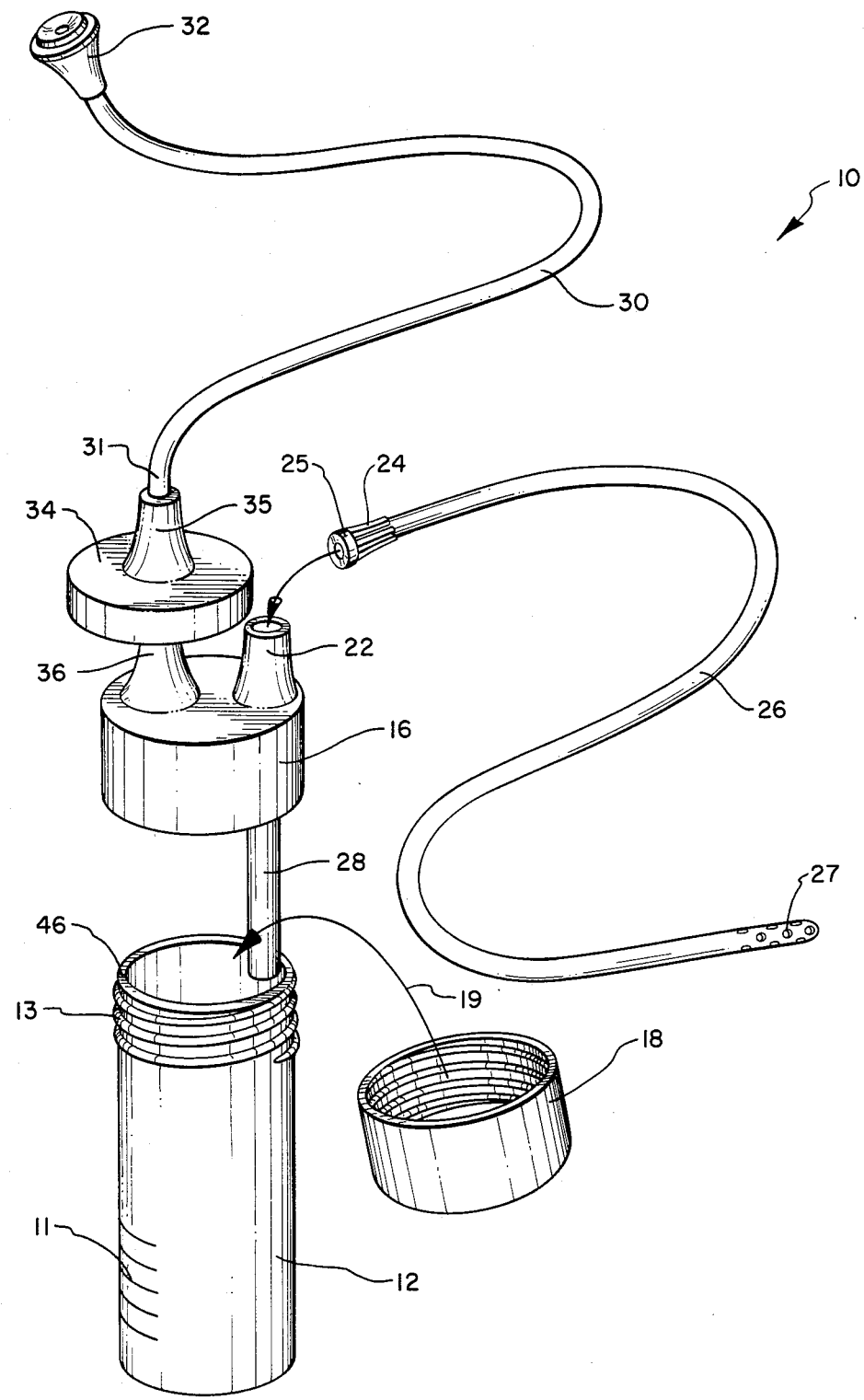
FIG. 2 is an exploded, perspective view of a first preferred embodiment of the pediatric suction system of this invention.

Referring now to FIGS. 1 and 2 of the drawing, a first preferred embodiment of the pediatric suction system of this invention is shown generally at 10 and includes a collection container 12 having a suction tube 26 connected at a fitting 22 at one end and a vacuum tube 30 connected to a cap 16 at the other end. Threads 13 on collection container 12 threadedly engage corresponding threads 17 inside cap 16 as well as similar threads (not shown) in closed cap 18 so as to securely engage the respective cap to collection chamber 12. Cap 16 includes a raised boss 36 having a filter 34 mounted thereto. An end 31 of vacuum tube 30 is mounted in sealing relationship to a corresponding raised boss 35 on the opposite side of filter 34. Collection container 12 is at least partially transparent and includes a plurality of indicia 11 on the wall. The spacing of indicia 11 is predetermined so as to indicate the volume of liquids aspirated into collection container 12.

Filter 34 is a conventional, liquid-impervious filter and is commercially available. Filter 34 is prepared from a hydrophobic material having submicron pores therethrough so as to allow the passage of gases while blocking any liquids. Since contact with liquids will effectively clog filter 34, it is provided with a serpentine-like entry on both faces so as to substantially impede contact of the filter media by liquids. Filter 34 is provided mechanical support mechanisms such as an open cellular foam material, grids, and the like, to maintain the structural integrity of the filter media. Since filter 36 is liquid impervious, it serves to block or otherwise prevent liquids aspirated through suction tube 26 from entering vacuum tube 30. Accordingly, a partial vacuum imposed on vacuum tube 30 draws aspirated liquids into collection container 12 through suction tube 26. While filter 36 prevents these liquids from being sucked into vacuum tube 30.

Filter 36 is mounted to cap 16 during assembly to form an integral unit along with vacuum tube 30 so that the entire unit consisting of cap 16, filter 36 and vacuum tube 30 can be removed from collection container 12. The advantage of this particular method of assembly is that after collection container 12 has received a sufficient volume of aspirated fluids as indicated by the fluid level (not shown) as determined by visual observation and by comparison to indicia 11, the entire assembly of vacuum tube 30, cap 16, and filter 36 may be removed from collection chamber 12. Closed cap 18 is placed thereon in sealing relationship to rim 46 as indicated schematically by arrow 19. Thus, closed cap 18 seals collection container 12 to securely contain any aspirated liquids. Collection container 12 thereby readily becomes a specimen container for transport of aspirated liquids directly to the hospital laboratory for analysis.

Suction tube 26 is a conventional catheter such as a gastric or endotracheal catheter and can be of any predetermined size, for example, a size number range from No. 3 to No. 5 French. The first end of suction tube 26 includes a plurality of apertures 28 therein while the second end is bonded to a conventional, suitable fitting 24 having an engagement means 25 on the end thereof. Fitting 24 engages a second fitting 22 on cap 16 by rim 25 engaging corresponding threads (not shown) in second fitting 22 in a tight, sealing relationship.

Advantageously, when suction tube 26 is used as an endotracheal suction catheter, fitting 24 can be removed from fitting 22 to permit the neonate 9 (FIG. 1) to breathe through suction tube 26 without the physician 8 having to remove suction tube 26 from the air passageway of neonate 9. Upon physician 8 observing a blockage in the airway of neonate 90 by detecting the cessation of the passage of air in and out through suction tube 26, it is a simple procedure for physician 8 to merely reconnect fitting 24 to second fitting 22 and again apply a partial vacuum to vacuum tube 30 by the application of his mouth 54 to mouthpiece 32.

Liquids aspirated through suction tube 26 are introduced into collection container 12 through a downcomer 28 which extends an incremental distance downwardly into collection container 12. Downcomer 28 reduces accidental aspiration of liquids (not shown) into vacuum tube 30 during the suction phase by introducing the liquids adjacent the lower end of collection container 12. This is an important feature since filter 36 is subject to plugging if wetted by the aspirated liquids, as discussed previously.

Figure 3:
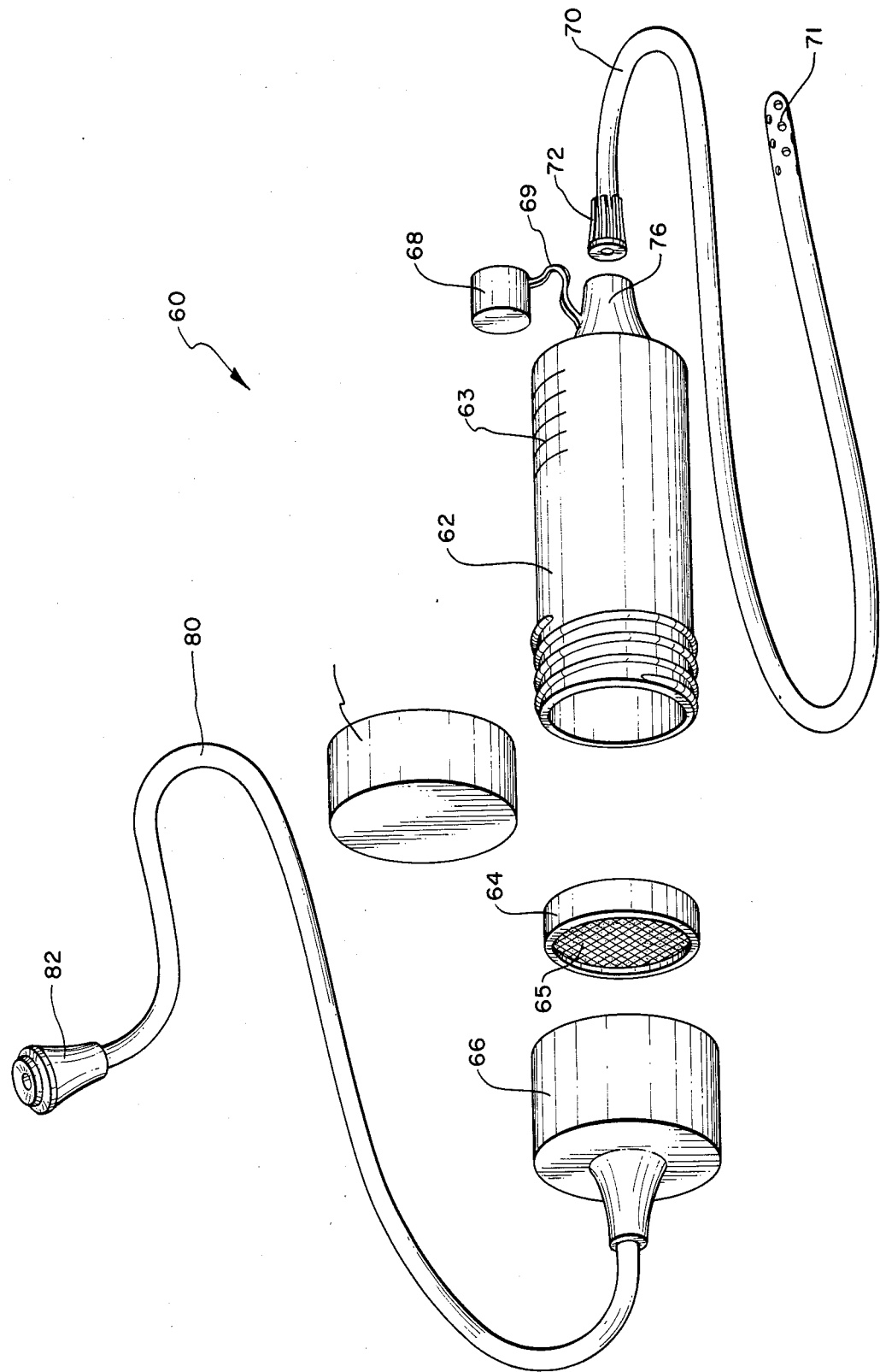
FIG. 3 is an exploded, perspective view of a second preferred embodiment of the pediatric suction system of this invention showing an alternate configuration for the liquid-impervious filter

Referring now to FIG. 3, a second preferred embodiment of the pediatric suction system of this invention is shown generally at 60 and includes a collection container 62 having a vacuum tube 80 attached at one end and a suction tube 70 releasably mounted by a fitting 72 adapted to matingly engage a second fitting 72 at the other end. Collection container 62 is prepared from a plastic material that is at least partially transparent and includes a plurality of indicia 63 which provide a general indication of the volume of aspirated fluids drawn into collection container 62.

A liquid-impervious filter 64 is provided from a conventional, liquid-impervious material 65 and is sealingly mounted inside cap 66, both of which are engaged against the rim of collection container 62. Filter 64 prevents aspirated liquids from entering vacuum tube 80 and also prevents any reverse transfer of matter from vacuum tube 80 to suction tube 70.

Suction tube 70 is removably mounted to a fitting 76 on collection container 62 so as to allow collection container 62 to be disconnected therefrom while allowing suction tube 70 to remain in place in neonate 9. A cap 68 is provided to seal fitting 76 while a flexible tether 69 secures cap 68 to fitting 76 to prevent loss of cap 68. The sealing relationship between cap 68 and fitting 76 may be any suitable system such as a friction fit, snap lock, or the like.

Importantly, filter 64 (similary to filter 34, FIG. 2) is sufficiently porous so that there is minimal interference with the transfer of the partial vacuum between physician 8 and neonate 9. This feature of being adequately porous is also important since physician 8 must be able to accurately gauge the degree of partial vacuum applied to the system without any significant interference from the respective filter (filter 14, FIGS. 2 and 3, or filter 64, FIG. 4).

The remaining features of pediatric suction system 60 such as apertures 71 in suction tube 70 and mouthpiece 82 on vacuum tube 80 are substantially identical to corresponding features found on suction catheter system 10 (FIGS. 1 and 2). In both instances the suction tube 26 (FIGS. 1 and 2) and suction tube 70 (FIG. 3) may be used either as endotracheal suction catheters or as gastric suction tubes as selectively determined by physician 8 (FIG. 1).

THE METHOD

The novel pediatric suction system of this invention is provided in a preassembled configuration in a sterilized package (not shown), as is conventional in the art. Physician 8 removes pediatric suction system 10 (FIGS. 1 and 1) or 60 from its sterilized package and inserts suction tube 26 or 70 into the air passageway or esophagus of neonate 9 at the desired location so as to provide oropharyngeal, endotracheal, or gastric suctioning. By lowering his mask 7, physician 8 is able to apply his lips 54 to mouthpiece 32 and gently apply suction to vacuum tube 30 or 80 the partial vacuum pressure of such suction is transmitted through the porous media of filter 34 or 64 into suction tube 26 or 70 so as to gently aspirate liquids from neonate 9. Advantageously, since suction tube 26 or 70 remains in place in neonate 9, any qualified operator such as a nurse or a respiratory therapist can promptly and efficiently operate the system.

Liquids aspirated through suction tube 26 or 70 are received inside collection container 12 or 62. Importantly and advantageously, filter 14 or 64 is fabricated from a commercially available, hydrophobic material which allows passage of gases but is impervious to liquids. Filter 14 or 64 thereby prevents any aspirated liquids (not shown) from being drawn into vacuum tube 30 or 80 and thus protects physician 8 from any pathogenic organisms that may be contained therein. Further, filter 14 or 64 prevents any viruses or organisms that may be contained in the secretions of physician 8 from entering suction tube 26 or 70 to the potential detriment of neonate 9.

Periodically during the delivery process, fitting 24 or 72 is removed from fitting 22 or 76 allowing neonate 9 to breathe normally through suction tube 26 or 70. A blockage or disturbance in the breathing of neonate 9 is promptly detected by physician 8 enabling him to easily and quickly reattach the appropriate fittings to again apply suction and aspirate liquids through suction tube 26 or 70. This procedure has the advantage of allowing physician 8 to leave suction tube 26 or 70 in place, thus avoiding the frequent removal and reinsertion of suction tube 26 or 70 with its corresponding trauma to the affected tissue of neonate 9.

Upon completion of the procedure or at any desired time, physician 8 may remove collection container 12 or 62 from the suction tube and seal the appropriate fitting with the plain cap provided. If it is desired to transport the aspirated liquids (not shown), it is a simple procedure to convert collection container 12 or 62 into a sample vial. Thereafter, physician 8 may reattach a second aspiration system to suction tube 26 or 70 to continue aspiration procedures as described previously.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured to United States Letters Patent is:

1. A pediatric suction system comprising:
   a cylindrical collection container having first and second opposed open ends with a first connector being in fluid communication with said first end, a cap covering said second end, a second connector being attached to said cap and being in fluid communication with said container, said container comprising a specimen collector having first and second closures respectively for said first end and said second end;
   a suction tube releasably mounted to said first connector on the first end of said container and in fluid communication with the container;
   a vacuum tube mounted to said cap on the second end of said container and in fluid communication with the container; and
   a liquid-impervious filter means interposed across said second open end of said container between said second connector and said container in blocking relationship between the suction tube and the second open end of the container.

2. A method for preventing operator aspiration of liquids during mouth-to-tube suction performed with a pediatric suction system comprising:
   preparing a container for receiving liquids by forming the container as a hollow cylinder with a fitting at a first end in fluid communication with said container, said fitting comprising a releasable coupling for releasably coupling a suction tube in fluid communication with said container, said container having a cap at a second end, the cap having a union means for joining a vacuum tube in fluid communication with said container;
   connecting said vacuum tube to said union means on said cap to provide fluid communication between said vacuum tube and the container;
   coupling a suction tube to said fitting to provide fluid communication between said suction tube and the container;
   interposing a liquid-impervious filter means across the open second end of the container comprising forming the filter means in a generally circular configuration and of a size selectively predetermined to be mounted across an open end of said container and being sealed against said open end of said container upon securing the cap to the container, said filter means preventing operator aspiration of liquids into said suction tube during mouth-to-suction tube suction.

3. The method defined in claim 2 wherein the coupling step comprises releasably attaching the suction tube to the fitting on the container thereby permitting removal of the container from the suction tube while leaving the suction tube in a location selected by the operator.

4. The method defined in claim 2 wherein the preparing step comprises forming the container as a sample collector wherein the connecting step comprises releasably mounting the cap and connected vacuum tube to the container and providing a second closure for the container after removal of the cap and connected vacuum tube from the container, the coupling step comprising releasably joining the suction tube to the fitting on the container and providing a first closure for the fitting on the container upon removal of the suction tube from the fitting on the container, the interposing step comprising mounting the filter means to the cap thereby removing the filter means from the container upon removing the cap from the container.

* * * * *